United States Patent [19]

Grandi et al.

[11] Patent Number: 4,987,078

[45] Date of Patent: Jan. 22, 1991

[54] PLASMID VECTORS FOR EXPRESSION IN *ESCHERICHIA COLI* AND/OR *BACILLUS SUBTILIS*

[75] Inventors: Guido Grandi, Segrate; Antonio Mele, Pavia; Elisabetta Colletti, Milan; Susanna Campagnoli, Codogno; Renzo Nogarotto, Motta di Livenza, all of Italy

[73] Assignee: Eniricerche S.p.A., Milan, Italy

[21] Appl. No.: 841,506

[22] Filed: Mar. 19, 1986

[30] Foreign Application Priority Data

Mar. 19, 1985 [IT] Italy ................................. 19960 A/85

[51] Int. Cl.$^5$ ...................... C12N 1/21; C12N 15/57; C12N 15/64; C12N 15/70; C12N 15/74
[52] U.S. Cl. .................................. 435/231; 435/69.1; 435/71.1; 435/91; 435/172.1; 435/172.3; 435/227; 435/252.3; 435/252.31; 435/252.33; 435/320.1; 435/832; 435/848; 536/27; 935/6; 935/8; 935/9; 935/10; 935/14; 935/22; 935/29; 935/38; 935/39; 935/41; 935/59; 935/72

[58] Field of Search ................ 435/317, 91, 68, 69.1, 435/71.1, 91, 172.1, 172.3, 227, 231, 252.3, 252.31, 252.33, 320, 848, 832; 536/27; 935/6, 84, 10, 14, 22, 29, 38, 39, 41, 59, 60, 61, 72, 73, 74

[56] References Cited

U.S. PATENT DOCUMENTS 4,626,510 12/1986 Grandi ............................... 435/317

OTHER PUBLICATIONS

Hawley et al. Nucleic Acids Research (1983) vol. 11, pp. 2237-2255.
Thomas et al. Gene 19 (1982) 211-219.
Gentz et al. PNAS 78-8 (1981) 4936-4940.
Flock et al. Mol. Gen. Geret 195(1984) 246-251.
Horinouchi et al. Mol. Gen. Genet 182 (1981) 341-348.

*Primary Examiner*—Richard A. Schwartz
*Assistant Examiner*—Richard C. Pert
*Attorney, Agent, or Firm*—Sughrue, Mion, Zinn, Macpeak & Seas

[57] ABSTRACT

Novel plasmid vectors are described, for expression in *Escherichia coli* and/or *Bacillus subtilis*, in which the gene which codes for a heterologous protein is placed under the control of a promoter of the erythromycin gene which permit the organisms transformed with the abovementioned plasmids to express the heterologous protein in high yields.

10 Claims, 5 Drawing Sheets

PLASMID VECTORS FOR EXPRESSION IN *ESCHERICHIA COLI* AND/OR *BACILLUS SUBTILIS*

The present invention relates to novel plasmid vectors for expression in *Escherichia coli* and/or *Bacillus subtilis*, in which the gene which codes for a heterologous protein is placed under the control of regulating sequences which permit the organisms transformed with the abovementioned plasmids to express the heterologous protein in high yields.

In particular, the present invention relates to the plasmid vectors pSM146 and pSM147 for expression in *E. coli*, in which the gene which codes for a heterologous protein is placed under the control of the terminating sequence of the phage fd of *E. coli* and of the pE194 erythromycin promoter modified by replacing the −35 region with segments of synthetic DNA.

The present invention further relates to the plasmid vector pSM143 for expression in *E. coli* and *B. subtilis* and useful for the formation of the plasmid vectors pSM146 and pSM147.

Recent developments in the field of genetic engineering have made it possible to prepare specific proteins by means of a process which includes the formation of a plasmid vector containing a heterologous gene which codes for a specific protein, to introduce the said vectors into host organisms, to isolate the said transformed organisms and to cultivate the same in culture media which are suitable for the purpose of obtaining the expression of the coded protein by the heterologous gene.

The expression "heterologous gene" designates a DNA which codes for a protein which is generally not produced by the host organisms which are used and which is referred to as a heterologous protein.

The term "expression" is used to indicate the process by which a protein is synthesized by an organism.

The said process takes place in two phases. The first, referred to as transcription, consists in the transfer of the genetic information from the DNA to the messenger RNA (mRNA). The second phase, referred to as translation, concerns the transfer of the information from the mRNA to the protein.

The transcription of the DNA into mRNA takes place by means of the enzyme RNA polymerase, and commences at a specific point of the DNA which is located in the vicinity of the sequence referred to as the promoter, and terminates at another well specified point, in the vicinity of the region of DNA defined as the terminator.

Because a specific heterologous protein is synthesized within a host cell, it is necessary to place the structural gene of the said protein under the control of specific sequences, i.e. the promoter, the terminator and the ribosomal binding site (RBS), which are recognized by the host organism and which permit the mRNA polymerase to transcribe the DNA into mRNA and permit the ribosomes and relevant enzymes to translate the mRNA into proteins.

It is well known that it is possible to obtain enhanced expression of a heterologous protein, by placing the structural gene of the protein under the control of a "strong" promoter.

A strong promoter is understood to be a promotor which exhibits specific sequences of nucleotide bases.

According to M. ROSemberg and D. Court (Am. Rev. Genet, 13 (1979), 319–353) the strong promoter sequence which is considered to be optimal is formed in the −35 region by the bases TTGACA and the −10 region by the bases TATAAT, with a spacer of 17–18 nucleotides between the two.

It is also well known that the maintenance of the said strong promoters on the plasmid vectors is dependent upon the simultaneous presence of a terminator which is as strong (R. Genko et al. PNAS 78, (1981) 4936–4940).

The terminator in fact determines the detachment of the RNA polymerase from the DNA molecule, thus preventing this from interfering with the processes of replication of the plasmid DNA. The absence of the terminator would cause a reduction in the number of copies of plasmids per cell and, consequently, the loss thereof from the cell progeny. Just like the promoters, the terminators are also defined, depending upon their sequence, as more or less strong, thus having a capacity to bring about the release of the RNA polymerase in a more or less effective manner.

Thus, in order to obtain good plasmid stability, a large number of copies of plasmids per cell and, in consequence, efficient expression of the heterologous protein, it is necessary that a strong promoter should be associated with an equally strong terminator. In the literature, the terminator of the phage fd of *E. coli* (K. Sugimoto et al., Nucleic Acids Res. (1978) 5, 4495–4503) is described as a particularly strong terminator. We have now found that, by modifying the erythromycin promoter of pE194, a plasmid present in *B. subtilis* BGSC 1E7, by replacing the −35 region with suitably designed segments of synthetic DNA, it is possible to obtain promoters which are stronger than that at the outset.

The said promoters are maintained in a stable state at the plasmid level by virtue of the simultaneous presence of the terminating sequence of the phage fd of *E. coli*, and the microorganisms transformed with the plasmid vectors containing the said promoters are capable of expressing the heterologous proteins with high efficiency.

In accordance with this, the scope of the present invention is constituted by novel plasmid vectors for expression in *E. coli* and/or *B. subtilis*, in which the gene which codes for a heterologous protein is placed under the control of regulating sequences which permit the organisms transformed with the abovementioned plasmids to express the heterologous protein in high yields.

In particular, the scope of the present invention is constituted by the plasmid vectors pSM146 and pSM147 for expression in *E. coli*, in which the heterologous gene which codes for a specific protein is placed under the control of the terminating sequence of phage fd of *E. coli* and of the pE194 erythromycin promoter modified by replacing the −35 region with segments of synthetic DNA.

The scope of the present invention is furthermore constituted by the plasmid vector pSM143 for expression in *E. coli* and *B. subtilis* and useful for the formation of the plasmid vectors pSM146 and pSM147.

The plasmid vector pSM143 may also be used for the formation of other plasmid vectors for expression, by replacing the region of the promoter and of the terminator with novel segments of synthetic DNA which code for other promoters and terminators.

According to the present invention, the segments of synthetic DNA in pSM146 and pSM147 exhibit the following sequences respectively:

5' CTG TTTTTTGTCAAT 3'
3' TCGAGAC AAAAAACAGTTAGATC 5' and

5' CTG TTTTTTGTCAACAACTTTTTT 3'
3' TCGAGAC AAAAAACAGTTGTTGAAAAAAGATC 5'

The said segments are synthesized according to well known techniques (J. H. Van Boom (1975) J. Biol. Chem. 250, 4592—R. L. Letsinger et al. (1975) J. Amer. Chem. Soc. 97, 32).

The plasmid vectors pSM146 and pSM147 introduced into cells of E. coli HBIOI are maintained in a stable state and impart to the cells transformed in this manner a resistance both to ampicillin and to kanamycin up to concentrations of 100 µg/ml and 15 µg/ml respectively.

The cells of E. coli transformed in this manner and cultivated in a suitable culture medium are capable of expressing the heterologous proteins in high yields. In accordance with the present invention in pSM143, pSM146 and pSM147 the gene which is placed under the control of the promoter-terminator sequences employed by us is that of the β-lactamase of pBR322 of E. coli (cf. J. G. Sutcliffe Proc. Natl. Acad. Sci. USA 75, 3737 (1978)).

Nevertheless, the selection of the gene to be cloned is not critical in relation to the invention, and use may be made of heterologous genes which code for other proteins such as, for example, human and animal hormones, proteins for use in foods, enzymes, etc.

According to the present invention, the plasmid vectors pSM146 and pSM147 are obtained from the plasmid pSM143 by replacing the SstI-XbaI region, having 740 base pairs, with the segments of synthetic DNA which are defined by the sequences set forth above.

The promoter sequence of pSM143 has a single SstI restriction site between the −35 region and the −10 region, and a single XbaI site upstream of the −35 region.

It is thus possible to replace the small segment (740 base pairs) carrying the promoter after digestion of the pSM143 with the specific restriction enzymes SstI and XbaI.

In accordance with the present invention, the plasmid pSM143 is obtained by a process which includes:

a. The formation, from the plasmid pSM110, of the plasmid pSM116, which exhibits a BamHI site in place of the PvuII site, b. The formation, from the pSM116, of the plasmid pSM131, which exhibits, downstream of the origin of replication, two restriction sites XhoI and BglII, which are useful for cloning, c. The insertion into the plasmid pUCB of the HindIII fragment containing the terminator of the phage of E. coli fd, and isolation of the plasmid pSM138, d. The isolation of the terminator of the phage fd from the plasmid pSM138 after digestion with the restriction enzyme BamHI, e. The insertion of the BamHi fragment containing the terminator of the phage fd into the BglII site of the plasmid pSM131 and isolation of the plasmid pSM137, f. The introduction of a HindIII site downstream of the structural gene of β-lactamase by means of in vitro mutation of the plasmid pSM116, and isolation of the plasmid pSM141, g. The ligation of the HindIII fragment of pSM141 containing the gene of β-lactamase with the HindIII fragment of 3500 base pairs of the plasmid pSM137 after digestion of the two plasmids with HindIII, and isolation of the plasmid pSM142, h. The ligation of the BamHI-EcoRI fragment of the plasmid pSM142 with the plasmid pSM112 after digestion of the two plasmids with the restriction enzymes BamHI and EcoRI, and isolation of the plasmid pSM143.

In accordance with the present invention, the gene cloned in the plasmid pSM143 is that of the β-lactamase of pBR322 of E. coli. Nevertheless, by deleting the EcoRI-HindIII fragment, of 850 base pairs, which contains the β-lactamase gene, it is possible to insert into the vector a gene coding for another protein, which will thus be under the control of regulating sequences (promoter, terminator and RBS) recognized both by E. coli and by B. subtilis.

According to the present invention, the process for the formation of the plasmid pSM143 provides for the formation of intermediate plasmids starting from the plasmid pSM110, which is obtained according to the description in Italian Patent Application No. 23.992 A/84 and the restriction map of which is reproduced in FIG. 1. The plasmid pSM110 exhibits an EcoRI site located upstream of the ATG of the β-lactamase gene of pBR322 of E. coli.

The plasmid pSM143 obtained in this manner exhibits, at the end of the β-lactamase gene, the terminator of the E. coli phage fd and, upstream of this, the erythromycin promoter of pE194, the sequence of which, in the −10 region, is in accordance with what is reported by M. Rosemberg et al., while the −35 region differs by two bases, exhibiting the sequence TTCATA.

The plasmid vector pSM143 may furthermore be maintained in a stable condition both in E. coli and in B. subtilis, in which it confers the resistance to ampicillin up to concentrations of 100 µg/ml and 5 µg/ml, and to kanamicin up to concentrations of 15 µg/ml and 5 µg/ml, respectively.

The plasmid pSM143 is characterized by the restriction map reproduced in FIG. 2.

In accordance with the present invention, the formation of the plasmid vectors pSM143, pSM146 and pSM147 is carried out in accordance with known techniques.

In particular, the digestion of the plasmids is undertaken by suspending the DNA plasmids in a solution containing 50 mM Tris-Hcl (pH 8.1), 50 mM NaCl and 10 mM $MgCl_2$ in the presence of the restriction enzyme or enzymes suitable for the purpose and under the conditions recommended for the purpose and under the conditions recommended by the supplier company.

The restriction enzymes used in the present invention were supplied by the companies BRL and BIOLABS. The ligase reaction of the fragments obtained after digestion is carried out by suspending the said fragments in a solution containing 50 mM tris.HCl, 10 mM $MgCl_2$, 10 mM dithiothreitol (DTTE and 1 mM ATP in the presence of the enzyme T4 DNA ligase.

The "in vitro mutation" reaction, the purpose of which is to modify in a controlled manner the sequence of bases of a specific region of DNA, is undertaken by using the methodology reported by M. I., Zoller et al. in Nucleic Acids Research 10 (1982) 6487–6500.

In order to verify the effect of the various promoters and of the terminator on the expression of the β-lactamase gene of pBR322, the plasmids of the present invention were introduced into *E. coli* HBIOI and *B. subtilis* BGSC 1A246 cells. The cells transformed in this manner were respectively cultivated in the following liquid media: LB (Bacto tryptone 10 g, yeast extract 5 g and NaCl 10 g) (DIFCO) and SMS (Spitizen minimal salts) with the addition of 0.5% glucose, 50 ug/ml tryptophan and trace elements, with agitation at 37° C., for about 6 hours. At the end of the said period, the -lactamase activity was determined in the cells for *E. coli*, and both n the cells and in the culture broth of *B. subtilis*, and compared with that obtained by cultivating cells of *B. Subtilis* NRRL B15896 containing the plasmid pSM119 obtained according to what is reported in Italian Application No. 84/23992. It can be seen from the results obtained that the plasmids pSM143 is stable in *B. subtilis* and *E. coli* and exhibits a β-lactamase activity which is twice as great as that of pSM119, both when introduced into *B. subtilis* and when introduced into *E. coli*.

On the other hand, the plasmids pSM148 and pSM147 prove to be stable only in *E. coli* and exhibit a β-lactamase activity from 6 to 65 times greater than that determined in the strain of *E. coli* containing pSM119.

The strains of *E. coli* HBIOI containing the plasmids pSM143, pSM136, pSM146 and pSM147 were deposited on Feb. 22, 1985 at the "American Type Culture Collection" Culture Centre respectively ATCC 53038, ATCC 53037, ATCC 53039 and ATCC 53040.

The experimental examples which follow are illustrative and do not limit the invention.

EXAMPLE 1

Formation of the plasmid pSM116

8 μg of the plasmid pSM110 is suspended in 20 μl of a solution containing 50 mM Tris.HCl, pH 8.1, 50 mM NaCl and 10 mM $MgCl_2$ (solution A) and di-gested with 1 unit (U) of restriction enzyme PvuII (BIOLABS) at 37° C. for 1 hour.

At the end of the reaction the enzyme is inactivated at 65° C. for 10 minutes.

ul of the reaction mixture obtained in this manner and 50 ng of phosphorylated BamHI linkers (BIOLABS) are bonded, in the presence of 1 U of enzyme T4 ligase, after addition to 19 μl of a solution containing 66 mM tris.HCl, pH 7.6, 6 mM $MgCl_2$, 10 mM dithiothreitol and 1 mM adenosine triphosphate (ATP) (solution B).

The ligase reaction is conducted at 14° C. for 14 hours.

The entire ligase mixture is then used to transform cells of *Escherichia coli* HBIOI rendered competent with $CaCl_2$ by the method described by Mandel and Higa (J. Mol. Biol. 53 (1970), 159–162). The selection of the transformed cells is undertaken by spreading on an L. Agar medium (10 g Bacto tryptone, 5 g YE and 10 g NaCl, 16 g Difco agar per liter of $H_2O$) containing 100 μg/ml ampicillin. In this manner it is possible to isolate only those cells containing the plasmid with the gene of ampicillin resistance ($Amp^R$).

Figure 5:
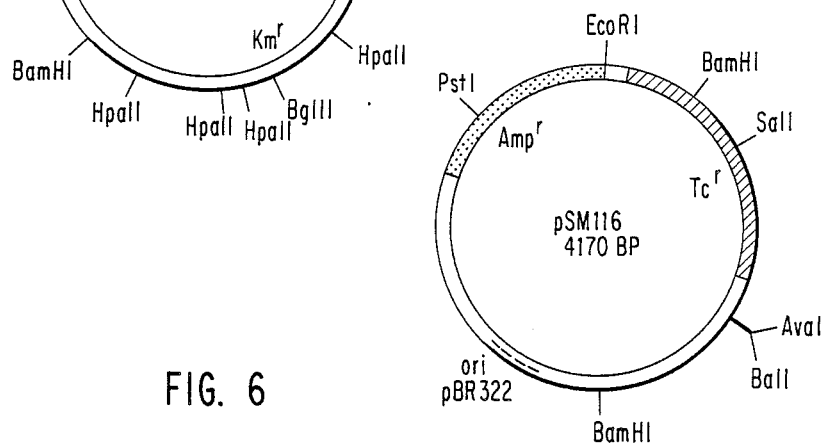
FIG. 5 shows the restriction map of the plasmid pSM116.

From an $Amp^R$ clone there is extracted and purified, according to the well known methods (cf.: Rodriquez et al. in "Recombinant DNA Techniques: an introduction" (1983) Addison-Wesley Publishing Company), the plasmid pSM116, the restriction map of which is reproduced in FIG. 5.

The plasmid pSM116 when compared with the plasmid pSM110 by means of electrophoresis on an agarose gel differs from the latter by the presence of a BamHI site in place of the PvuII site.

EXAMPLE 2

Formation of the plasmid pSM131

2 μg of the plasmid pSM116, obtained as stated in example 1, are diluted in 50 ul of solution A and digested with 2 U of restriction enzyme PstI (BIOLABS).

At the end of the digestion reaction 50 ul of $H_2O$ and 100 μl of phenol are added to the mixture.

The phenol is then extracted from the aqueous phase with an equal volume of ether, and DNA is precipitated by addition of 1/10 of the volume of a 3M solution of sodium acetate (pH 5.5) and 2.5 volumes of 95% ethanol, at a temperature of −70° C. for 10 minutes.

The DNA precipitated in this manner is separated from the solution by centrifuging at 10,000 revolutions per minute for 10 minutes and is then resuspended in 30 μl of Solution A in the presence of 0.6 U of enzyme Bal 31.

The digestion reaction is conducted at 23° C. for 6 minutes. The DNA linearized in this manner is precipitated and separated from the reaction mixture in the manner as stated above.

The plasmid DNA is resuspended in 20 μl of $H_2O$ and 1 μl of the said aqueous solution (50 ng of DNA) is bonded to 50 ng of DNA of the XhoI linker (Wortington) in the presence of 0.1 U of T4 ligase, after suspension in 10 μl of solution B in the manner stated in example 1.

The XhoI linkers had previously been phosphorylated at the terminal 5' position according to the description in "Molecular Cloning, A Laboratory manual" (Ed. T. Maniatis, E. F. Fritsch, J. Sambrook (1982) Cold Spring Harbor Laboratory).

The DNA of the XhoI linkers, the sequence of which is the following:

TCTCGAGA

AGAGCTCT, when it polymerizes, generates the recognition site for the enzyme BglII TCTCGAGATCTCGAGA
AGAGCTCTAGAGCTCT
|———————|
BglII.

If at least two XhoI linkers are then bonded to the DNA of the plasmid pSM116, cut with PstI and treated with Bal31, the result will be the formation of a construct which will exhibit two new restriction sites: XhoI and BglII. 10 μl of the ligase mixture are used to transform cells of E. coli HBIOI rendered competetent as described previously (Example 1). The cells are selected for tetracycline resistance and ampicillin sensitivity by spreading on an L agar medium containing 20 μg/ml of tetracycline.

The plasmids are extracted from the 44 Tc$^R$ and Amp$^S$ clones by the rapid procedure.

The plasmid DNAs obtained in this manner are digested with 1 U of enzyme XhoI after suspension in 20 μl of solution A, for the purpose of verifying the completion of the insertion of the linker.

After analysis on an agarose gel (7%) the plasmids linearized with XhoI and with reduced lengths as compared with pSM116 were subsequently analysed for the purpose of verifying the presence of the BglII restriction site. The plasmid containing both the BglII and the XhoI restriction site and having a reduced length as compared with pSM116 was designated pSM131.

The regions in proximity to the BglII site of the BglII-BamHI fragments of the plasmid pSM131 are sequenced by the method of Maxam and Gilbert (Methods in Enzymology, vol. 65, pp. 499–560 (1980)).

Figure 6:
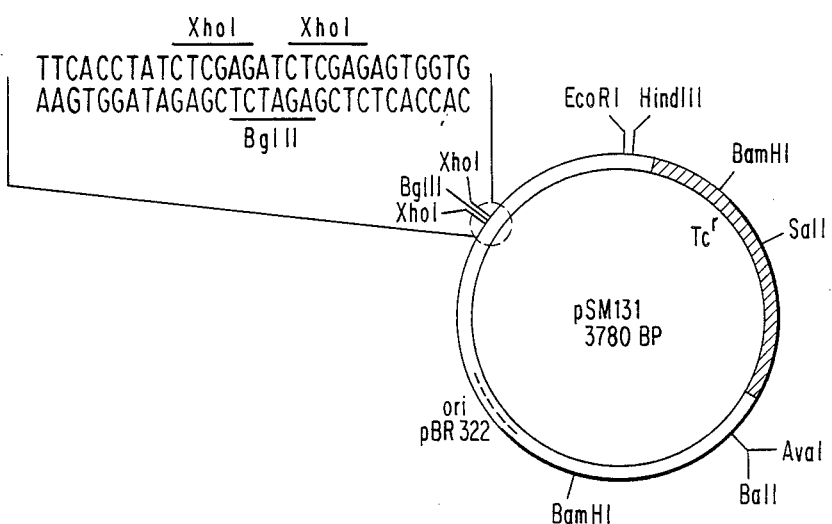
FIG. 6 shows the restriction map of the plasmid pSM131 and the precise arrangement of the two XhoI linkers.

FIG. 6 shows the restriction map of the plasmid pSM131 and the precise arrangement of the two XhoI linkers. The said linkers are situated at a distance of 69 bases from the stop codon (TAA) of β-lactamase (position 3224 of pBR322) and at 532 bases from its start codon (ATG) (position 3618 of pBR322), thus indicating that the enzyme Bal31 has deleted approximately 390 base pairs (bp) from the PstI site towards the origin of replication and only 5 bp from the PstI site towards the EcoRI site. Accordingly, the plasmid pSM131 exhibits the expected characteristics, possessing the XhoI and BglII restriction sites a short distance downstream of the origin of replication of pBR322.

EXAMPLE 3

Cloning of the Terminator of the Phage fd in pUC8 and Formation of the Plasmid pSM138

1 μg of the plasmid pUC8 (Boehringer-Mannheim) and 1 μg of the plasmid pLUB3 of E. coli are each digested with 1 U of restriction enzyme HindIII (BIOLABS) after suspension in 20 μl of solution A.

Whereas the pUC8 is linearized from the cut with HindIII, the pLUB3 is cut into two segments, the smaller of which, of approximately 352 bp, contains the terminating sequence of the phage fd.

The plasmid DNAs are precipitated and separated from the reaction mixtures in the manner stated previously.

60 ng of pLUB3-HindIII and 15 ng of pUC8-HindIII are suspended in 10 μl of solution B and bonded together in the presence of 0.1 U of T4 ligase.

2 μl of ligase mixture are utilized for the purpose of transforming suitable cells of E. coli JM83 (BRL).

The transformants are selected for resistance to ampicillin by spreading on an L-agar medium (DIFCO) containing 100 μg/ml of ampicillin and the indicator X-gal in the manner described by J. Messing (Methods in Enz. vol. 101 (1983) pp. 20–78).

12 white colonies are obtained in this manner, from which the plasmids are extracted by the rapid procedure. 8 of the said plasmids are composed of the DNA of pUC8 and of the HindIII fragment of pLUB3 containing the terminator of the phage fd.

In the HindIII fragment of the terminator a BamHI site is located at a distance of only 4 bases from one of the HindIII ends. Since a BamHI site is also present on the pUC8 at a distance of a few bases from the HindIII site, it is possible to isolate the terminator of the hybrid plasmids obtained in this manner by digestion with the enzyme BamHI, provided that the orientation of the HindIII fragment of the terminator in pUC8 is such that the two BamHI sites are in distal positions.

The hybrid plasmids are then digested with BamHI and the DNA separated on 7.5% acrylamide gel.

After staining with ethidium bromide and visualization of the DNA under UV light, it is observed that two of the eight plasmids analysed exhibited, after the cut with BamHI, two segments of DNA, one of approximately 350 bp and the other having the length of pUC8.

Figure 7:
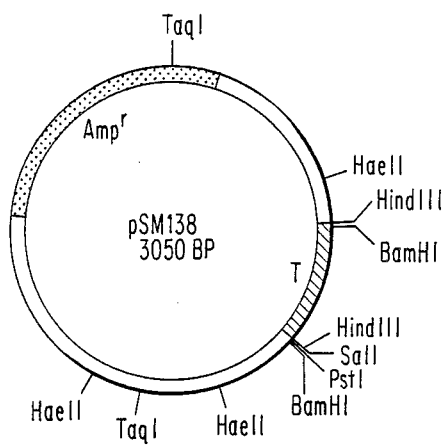
FIG. 7 shows the restriction map of the plasmid pSM138 and the precise orientation of the Hind III fragment containing the terminator of the *E. coli* phage fd.

The restriction map of one of these plasmids, which are designated pSM138, is reproduced in FIG. 7.

EXAMPLE 4

Insertion of the Terminator into the Plasmid pSM131 and Formation of the Plasmid pSM137

1 μg of pSM131 and 3.5 μg of pSM138 obtained as stated in examples 2 and 3 are digested, respectively, with 1 U of enzyme BglII and 3.5 U of BamHI, after suspension in 20 μl of solution A.

At the end of the reaction, the enzymes are inactivated at 65° C. for 10 minutes.

2 μl of the reaction mixtures are added to 20 μl of solution B and bonded with 0.1 U of T4 ligase.

Since the enzymes BamHI and BglII generate, after cutting of the DNA, cohesive ends which can be bonded together, it is possible to obtain hybrid molecules formed from the pSM131 and from the small BamHI fragment of the pSM138 containing the terminator of the phage fd.

2 μl of the ligase mixture are used for the purpose of transforming suitable cells of E. coli HBIOI.

The transformants are then selected on plates of L agar containing 20 μg/ml tetracycline.

Figure 8:
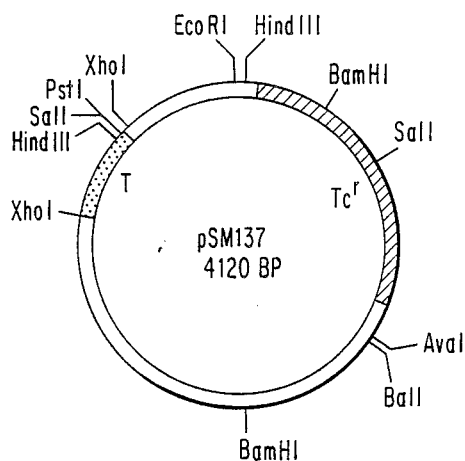
FIG. 8 shows the restriction map of the plasmid pSM137 and the arrangement of the terminator of the phage fd before the origin of replication of the plasmid (in the anticlockwise direction).

Among the Tc$^R$ clones obtained in this manner, one was isolated, bearing the hybrid plasmid pSM137, the restriction map of which is reproduced in FIG. 8.

The said plasmid is composed of the pSM131 and of the small BamHI fragment of pSM138 containing the terminator of the phage fd which is thus located before (in the anticlockwise sense) the origin of replication of the plasmid.

EXAMPLE 5

Introduction of the HindIII Site After the Structural Gene of β-lactamase, and Formation of the Plasmid pSM141

1 μg of the phage M13 mp9 having a double helix (RF) and 1 μg of pSM116, obtained as stated in example 1, are digested, respectively, with 1 U of enzyme EcoRI and 1 U of enzyme BamHI, after suspension in 20 μl of reaction mixture A, under the conditions recommended by the supplier company Biolabs. After inactivation of the enzyme at 65° for 10 minutes, 1 μl of each of the two mixtures are bonded together, after suspension in 20 μl of reaction mixture B, in the presence of 0.1 U of T4 ligase.

5 μl of ligase mixture are then used for the purpose of transforming suitable cells of E. coli JM83, selection being carried out by resistance to ampicillin. The DNA (RF) of the phages is prepared from twelve of the white plaques obtained in this manner, as described by M. Zoller and M. Smith (Nucl. Ac. Res. 10 (1982) 6487–6500).

The DNAs are then digested with the enzymes BamHI and EcoRI as stated previously, and the samples are separated on 0.8% agarose gel.

Two of the hybrid molecules obtained in this manner prove to be formed by the DNA of the phage M13 mp9 and by the segment of 2000 bp of the plasmid pSM116 bearing the gene of β-lactamase.

From one of the two plaques there is then prepared the single-helix form of the recombinant phage DNA, purified as described by Zoller and Smith (Nucl. Ac. Research 10 (1982) 6487–6500).

A synthetic oligonucleotide of 18 bases was then designed to be complimentary to the DNA region which follows the end of the gene of β-lactamase, apart from one base, and the sequence of which is the following:

```
5'TAACTGTCAGACCAAGTTTACTCATATAT-3'
    GTCTGGTTC AATGAGTA 5' synthetic primer
              G
           ‾‾‾‾‾‾
           HindIII
```

The single-helix DNA of the recombinant phage, the universal primer TCCCAGTCACGACGT (Biolabs) and the synthetic oligonucleotide (synthesized by Creative Biomolecules—San Francisco—Ca) are used for the experimental investigation of in vitro mutation as described by K. Norris et al. (Nucl. Ac. Research II (1983) 5103–5112), for the purpose of positioning a HindIII site after the end of the gene of β-lactamase.

For the purpose of the in vitro polymerization and ligation reaction, the reaction mixture is treated with 3 U of BamHI and 3 U of EcoRI under the conditions recommended by the supplier company (Biolabs). The DNA is then separated on 0.8% agarose gel, and the EcoRI-BamHI fragment of 2000 bp, which is visible under UV light after staining with ethidium bromide, is eluted in the manner described in Molecular Cloning. A laboratory Manual, Ed. T. Maniatis, E. F. Fritsch, J. Sambrook (1982) Cold Spring Harbor Laboratory.

100 ng of the segment of DNA eluted in this manner and 50 ng of the EcoRI-BamHI fragment, of approximately 350 bp, of the plasmid pSM116, recovered from 7.5% acrylamide gel according to the procedure described by Maxam and Gilbert in Methods in Enzymology vol. 65 (1980) 526–527, are bonded in the presence of 0.1 U of T4 ligase, after suspension in 50 μl of reaction mixture B. 10 μl of ligase mixture are used for the purpose of transforming suitable cells of E. coli HBIOI, selecting the transformants for resistance to ampicillin (100 μg/ml).

The plasmid DNA is prepared from four $Amp^R$ clones according to the rapid procedure.

The DNA preparations are then treated with 1 U of enzyme HindIII in 30 μl of reaction mixture A.

In the case of complete mutation, it was expected that the cutting with the said enzyme would generate two fragments of DNA, one of 860 bp and the other of 1600 bp.

The analysis, on 1% agarose gel, of the four samples obtained as stated above indicated that two of these exhibited the expected characteristics.

One of the said plasmids was designated pSM141.

Figure 9:
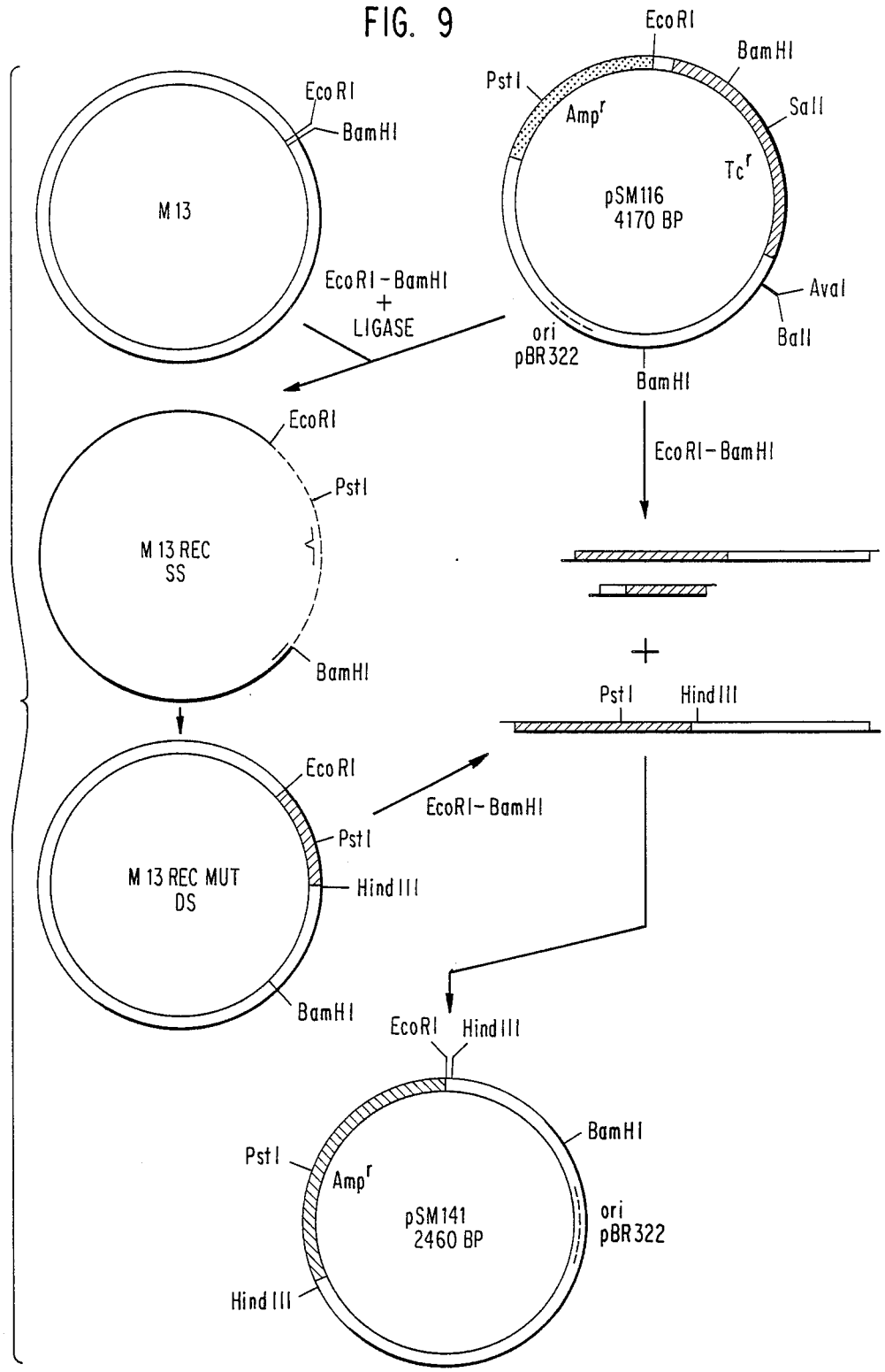
FIG. 9 shows the restriction map of pSM141 and the stages (in vitro mutation) for preparation thereof.

Its restriction map and the steps required for the preparation thereof are reproduced in FIG. 9.

EXAMPLE 6

Formation of the Plasmid pSM142

1 μg of the plasmid pSM141 and 1 μg of the plasmid pSM137, which was obtained as stated in example 4, are each digested with 1 U of enzyme HindIII, after suspension in 20 μl of solution A.

The enzyme HindIII cuts the plasmid pSM141 at two points, generating two fragments, one of 830 bp and the other of 1600 bp. The pSM137 also exhibits two HindIII sites, and thus the digestion thereof gives rise to a fragment of 550 bp and to one of 3500 bp (FIG. 8).

1 μl of each reaction mixture is added to 18 μl of solution B containing 0.1 U of enzyme T4 ligase. The ligase reaction is carried out at 14° C. for 14 hours.

After inactivation of the enzyme at 65° for 10 minutes, 5 μl of ligase mixture are used for the purpose of transforming suitable cells of E. coli HBIOI.

The transformants are selected for resistance to ampicillin and to tetracycline, by spreading on an L agar medium containing 100 μg/ml of ampicillin and 20 μg/ml of tetracycline.

From a $Tc^R$, $Amp^R$ clone there is isolated by the rapid procedure a plasmid formed by the fragment of approximately 830 bp of the pSM141 and by the fragment of approximately 3500 bp of the pSM137.

Figure 10:
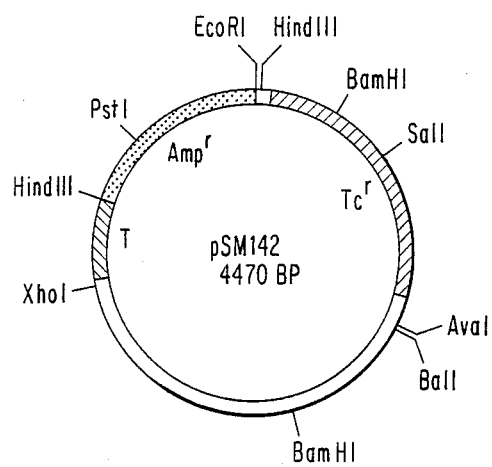
FIG. 10 shows the restriction map of the plasmid pSM142.

The plasmid, the restriction map of which is represented in FIG. 10, was designated pSM142.

EXAMPLE 7

Formation of the Plasmid pSM143

Figure 11:
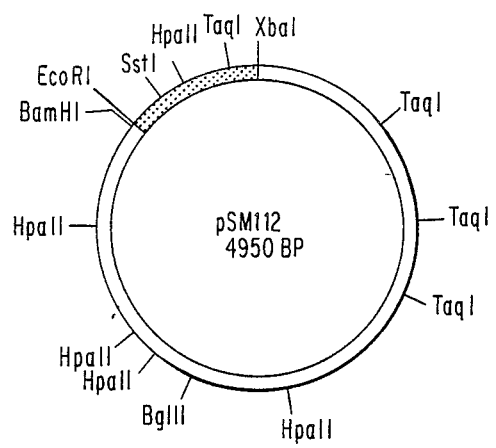
FIG. 11 shows the restriction map of the plasmid pSM112.

1 μg of the plasmid pSM142 and 1 μg of the plasmid pSM112, which was obtained as stated in Italian Patent Application No. A/82 23992 and represented in FIG. 11, are suspended in 20 μl of solution A and simultaneously cut with 1 U of enzyme BamHI and 1 U of enzyme EcoRI at 37° C. for 1 hour.

After inactivation of the enzymes at 65° for 10 minutes, 1 μl of the reaction mixture is used for the ligation reaction in the presence of T4 ligase as previously described.

The entire ligase mixture is then employed for the purpose of transforming suitable cells of E. coli HBIOI, selecting the transformants for resistance to ampicillin and to kanamycin on plates of L agar containing 100 μg/ml of ampicillin and 15 μg/ml of kanamycin.

Figure 1:
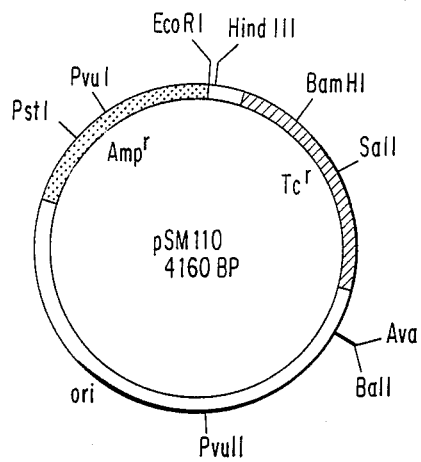
FIG. 1 shows the restriction map of the plasmid pSM110.
Figure 2:
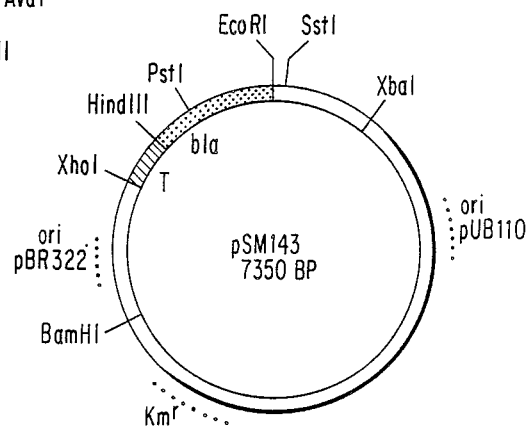
FIG. 2 shows the restriction map of the plasmid pSM143.

From an Amp$^R$ and Km$^R$ clone there is isolated by the rapid procedure the plasmid pSM143, the restriction map of which is reproduced in FIG. 2.

The pSM143 is composed of the 4950 bp fragment of the pSM112 and of the 2400 bp fragment of the pSM142.

The plasmid pSM143 is then employed for the purpose of transforming cells of *B. subtilis* SMS003 NRLL B 15897, which are rendered competent as described by Contente and Dubnau (Mol. Gen. Genet. 167(1979) 251-258).

The selection of the transformants is carried out by spreading on tryptose blood agar base (TBAB) medium from DIFCO containing 5 μg/ml of kanamycin.

Plasmids identical to pSM143 were isolated from the Km$^R$ clones, thus indicating that the said plasmid was maintained in a stable condition in cells of *B. subtilis*.

EXAMPLE 8

Formation of the Plasmid pSM146

1 μg of the plasmid pSM143 is digested simultaneously with 1 U of enzyme SstI and 1 U of enzyme XbaI in 20 μl of solution A at 37° C. for 1 hour.

Figure 3:
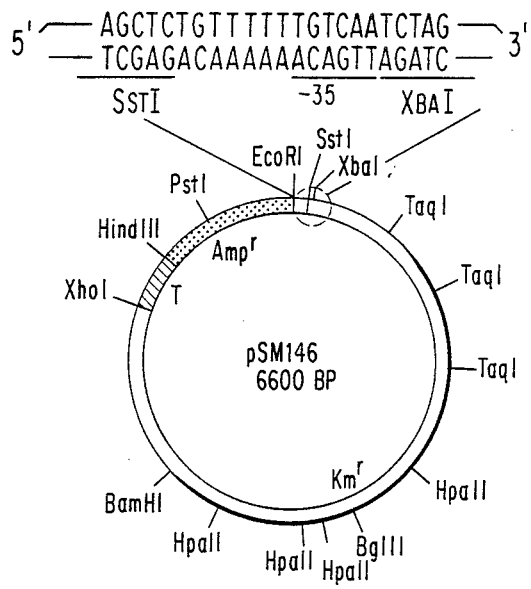
FIG. 3 shows the restriction map of the plasmid pSM146 and the sequence of the fragment of synthetic DNA present in the −35 region of the promoter.

After inactivation of the enzymes at 65° for 10 minutes, 1 μl of the reaction mixture is added to 19 μl of the solution B containing 0.1 U of T4 ligase and 50 ng of the fragment of synthetic DNA, the sequence of which is reproduced in FIG. 3.

The ligase reaction is carried out at 14° C. for 14 hours.

After inactivation of the enzyme at 65° for 10 minutes, 5 μl of the ligase mixture are used for the purpose of transforming suitable cells of *E. coli* HBIOI. The selection of the transformants is then undertaken on plates of L agar containing 100 μg/ml of ampicillin. From an Amp$^R$ clone there is isolated by the rapid procedure a plasmid in which the fragment SstI-XbaI of 740 bp of the pSM143 was replaced by the segment of synthetic DNA of 15 bp+8 single bases. The new plasmid is designated pSM146, and its restriction map is reproduced in FIG. 3.

EXAMPLE 9

Formation of the Plasmid pSM147

Figure 4:
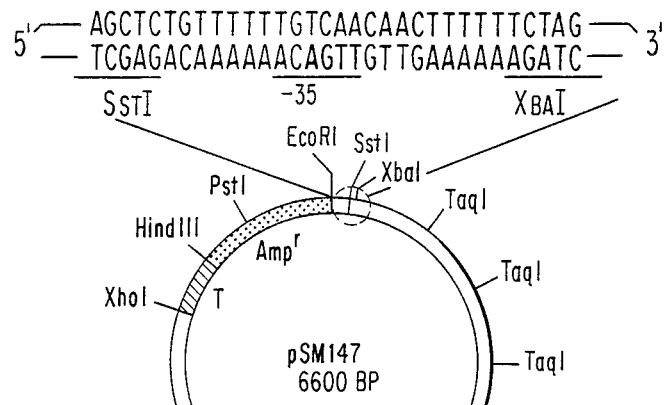
FIG. 4 shows the restriction map of the plasmid pSM147 and the sequence of the fragment of synthetic DNA present in the −35 region of the promoter.

The procedure is carried out as in example 8 above, using in the ligase reaction 50 ng of a segment of synthetic DNA whose sequence is reproduced in FIG. 4.

The plasmid isolated from an Amp$^R$ clone, designated pSM147, exhibits, in comparison with the pSM143, the replacement of the SstI-XbaI fragment by the synthetic segment of 24 bp+8 single bases.

The restriction map of the plasmid pSM147 is reproduced in FIG. 8.

EXAMPLE 10

Determination of the β-lactamase Activity of pSM143, pSM146 and pSM147

Cells of *E. coli* HBIOI and *B. subtilis* BGSC 1A246, containing the plasmids pSM143, pSM146, pSM147 and pSM119 (comparison), are cultivated in conical flasks having a capacity of 250 ml, each containing 25 ml of culture medium previously sterilized at 120° for 15 minutes.

*B. subtilis* is cultivated in SMS (Spitizen Minimal Salts) medium to which is added glucose (0.5%), tryptophan (50 μg/ml) and trace elements.

*E. coli* is cultivated in LB. (DIFCO) medium.

The conical flasks are incubated, with agitation, at 37° C. for 6 hours.

The production of β-lactamase is determined, for *E. coli*, in the periplasmic specimens obtained as described by A. Nicolaidis et al. (J. Bacteriol. 135 (1978), 178) and, for *B. subtilis*, both in the supernatant liquid and in the sonicated cells. In order to prepare the sonicated cells, 5 ml of the B. subtilis culture are centrifuged at 5000 rpm for 10 minutes. The cells obtained in this manner are suspended in 5 ml of solution containing 30 mM tris. HCl, pH 7.2, and 50 mM NaCl and centrifuged again at 5000 rpm for 10 minutes.

The cells are then suspended in 5 ml of 100 mM phosphate buffer, pH 7.0, and treated 3 times (for 1 minute each time) with an MSE sonicator, Soniprep model 150, operating at maximum intensity.

The β-lactamase activity is measured with Nitrocefin as described by O'Callaghan et al. (Antimicrob. Ag. Chemother. I (1972) 283-288).

1 unit of β-lactamase is defined as the quantity of enzyme required to hydrolyse 1 nanomole of substrate per minute at 37° C.

Table I shows the figures for β-lactamase activity which were determined in the various cultures of *B. subtilis* BGSC 1A246 and *E. coli* HBIOI.

TABLE I

| | β-LACTAMASE ACTIVITY (U/ml) | |
|---|---|---|
| PLASMID | *E. coli* HB101 | *B. subtilis* BGSC 1A246 |
| pSM119 | 1300 U/ml | *380 U/ml |
| pSM143 | 2000 U/ml | *700 U/ml |
| pSM146 | 12000 U/ml | — |
| pSM147 | 85000 U/ml | — |

*Total of the activity determined in the supernatant liquid and in the sonicated cells.

We claim:

1. A plasmid vector useful for the expression of a heterologous protein in *Escherichia coli* wherein said plasmid vector comprises, in sequential order,
   (1) a modified pE194 erythromycin promoter,
   (2) a gene encoding for a heterologous protein, and
   (3) the terminator of phage fd of *Escherichia coli*, wherein said modified pE194 erythromycin promoter comprises a pE194 erythromycin promoter having the −35 region thereof replaced by sequence (I) or (II) below:

5' CTGTTTTTTTGTCAAT 3'          (I)
   3' TCGAGACAAAAAACAGTTAGATC 5'

5' CTGTTTTTTTGTCAACAACTTTTTT 3'  (II)
   3' TCGAGACAAAAAACAGTTGTTGAAAAAAGATC 5'.

2. The plasmid vector according to claim 1, wherein said heterologous protein is selected from the group consisting of human hormones, animal hormones, proteins for use in foods and enzymes.

3. The plasmid vector according to claim 2, wherein said heterologous protein is the enzyme β-lactamase.

4. A process for obtaining a plasmid vector useful for the expression of a heterologous protein in *Escherichia coli*, comprising the steps of:
   (1) digesting plasmid vector pSM143 with restriction enzymes SstI and XbaI, and (2) replacing the 740 base pair SstI-XbaI sequence comprising a portion of the promoter of plasmid vector pSM143 with sequences (I) or (II) below:

5' CTGTTTTTTGTCAAT 3'  (I)
3' TCGAGACAAAAAACAGTTAGATC 5'

5' CTGTTTTTTGTCAACAACTTTTTT 3'  (II)
3' TCGAGACAAAAAACAGTTGTTGAAAAAAGATC 5'.

5. The process claimed in claim 4, wherein said plasmid vector pSM143 is produced by the process comprising the steps of:
  (1) replacing the PvuII site of plasmid pSM110 with a BamHI site so as to obtain plasmid pSM116,
  (2) replacing the PstI site of pSM116 with an XhoI-BglII-XhoI site so as to obtain plasmid pSM131,
  (3) inserting the HindIII fragment of plasmid pLUB3, which contains the terminator sequence of phage fd of *Escherichia coli*, into the HindIII site of pUC8 so as to obtain plasmid pSM138,
  (4) digesting plasmid pSM138 with BamHI so as to isolate the terminator of phage fd of *Escherichia coli* therefrom,
  (5) inserting the resulting BamHI fragment of step (4) into the BglII site of pSM131 so as to obtain plasmid pSM137,
  (6) introducing a HindIII site downstream of the β-lactamase gene in plasmid pSM116 by in vitro mutation so as to obtain plasmid pSM141,
  (7) ligating the HindIII fragment of pSM141, which contains the β-lactamase gene, and the 3500 base pair HindIII fragment of plasmid pSM137 so as to obtain plasmid pSM142, and
  (8) ligating the BamHI-EcoRI fragment of plasmid pSM142 into the BamHI site of plasmid pSM112 so as to obtain plasmid vector pSM143.

6. A process for the production of β-lactamase comprising:
  (1) transforming a host microorganism with a plasmid vector selected from the group consisting of pSM143, pSM146 and pSM147,
  (2) isolating the resulting transformed microorganisms, and
  (3) cultivating the resulting transformed microorganisms in a liquid culture medium containing sources of carbon, sources of nitrogen and trace elements so as to obtain β-lactamase from said transformed microorganisms.

7. The process according to claim 6, wherein said host microorganism is selected from the group consisting of *Escherichia coli* HB101 and *Bacillus subtilis* BGSC 1A246.

8. *Escherichia coli* (pSM143) ATCC 53038
9. *Escherichia coli* (pSM146) ATCC 53039
10. *Escherichia coli* (pSM147) ATCC 53040

* * * * *